United States Patent

Gayer et al.

Patent Number: 5,773,445
Date of Patent: Jun. 30, 1998

[54] 3-METHOXY-PHENYL-ACRYLIC ACID METHYL ESTERS

[75] Inventors: Herbert Gayer, Monheim; Peter Gerdes, Aachen; Otto Schallner, Monheim; Stefan Dutzmann, Hilden; Heinz-Wilhelm Dehne, Bonn; Gerd Hänssler, Leverkusen, all of Germany

[73] Assignee: Bayer Aktiengesellschaft, Leverkusen, Germany

[21] Appl. No.: 649,594

[22] PCT Filed: Nov. 14, 1994

[86] PCT No.: PCT/EP94/03773

§ 371 Date: May 20, 1996

§ 102(e) Date: May 20, 1996

[87] PCT Pub. No.: WO95/14674

PCT Pub. Date: Jun. 1, 1995

[30] Foreign Application Priority Data

Nov. 25, 1993 [DE] Germany .......................... 43 40 181.3

[51] Int. Cl.$^6$ ...................... C07D 239/34; C07D 239/70; C07D 403/12; A01N 43/54
[52] U.S. Cl. .......................... 514/269; 514/212; 514/241; 514/246; 514/248; 514/249; 514/252; 514/259; 540/601; 544/295; 544/296; 544/238; 544/319; 544/180; 544/212; 544/216; 544/219

[58] Field of Search ...................................... 544/319, 295, 544/216; 514/269, 212, 249, 259; 540/601

[56] References Cited

FOREIGN PATENT DOCUMENTS

| 382375 | 8/1990 | European Pat. Off. . |
| 391451 | 10/1990 | European Pat. Off. . |

*Primary Examiner*—John M. Ford
*Attorney, Agent, or Firm*—Sprung Kramer Schaefer & Briscoe

[57] ABSTRACT

The application describes new 3-methoxy-2-phenyl-acrylic esters of the formula (I)

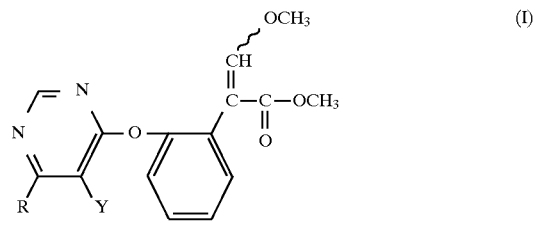

in which

R and Y have the meanings given in the description, a process for their preparation, and their use as pesticides.

5 Claims, No Drawings

3-METHOXY-PHENYL-ACRYLIC ACID METHYL ESTERS

This is a 371 of PCT/EP94/03773, filed Nov. 14, 1994, published as WO95/14674 Jun. 1, 1995.

The invention relates to new methyl 3-methoxy-2-phenyl-acrylates, to a process for their preparation, and to their use as pesticides.

It is known that certain methyl 3-methoxy-acrylates, such as, for example, the compound methyl 3-methoxy-2-(6-phenyl-2-pyridylthio)-acrylate or the compound methyl 3-methoxy-2-[N-(6-phenyl-2-pyridyl)-N-methyl-amino]-acrylate or the compound methyl 3-methoxy-2-[5-(4-chlorphenyl)-3-pyridyloxy]-acrylate, have fungicidal properties (cf. for example EP 383 117).

However, the activity of these previously known compounds is not entirely satisfactory in all sorts of applications, in particular when low application rates and concentrations are used.

New methyl 3-methoxy-2-phenyl-acrylates of the general formula (I)

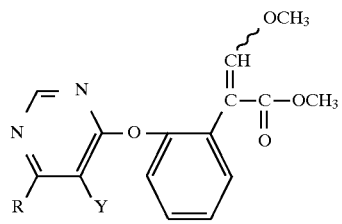

(I)

in which

Y represents fluorine, chlorine, bromine or iodine,

R represents halogen or a radical of the formula Ar—Z—, in which

Ar represents optionally substituted aryl or heteroaryl and

Z represents oxygen, sulfur or a group of the formula —S(O)—, —SO$_2$—, —NH—, —N(CH$_3$)—, —CH$_2$O— or —CH$_2$S—, have been found.

If appropriate the compounds of the formula (I) can exist in the form of geometric isomers or variously composed isomer mixtures. The invention claims both the pure isomers and the isomer mixtures.

Furthermore, it has been found that the new methyl 3-methoxy-2-phenyl-acrylates of the general formula (I)

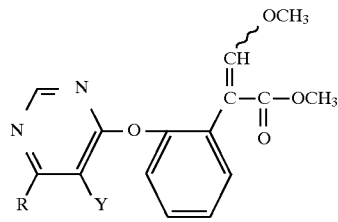

(I)

in which

Y represents fluorine, chlorine, bromine or iodine,

R represents halogen or a radical of the formula Ar—Z—, in which

Ar represents optionally substituted aryl or heteroaryl and

Z represents oxygen, sulfur or a group of the formula —S(O)—, —SO$_2$—, —NH—, —N(CH$_3$)—, —CH$_2$O— or —CH$_2$S—, are obtained when a)

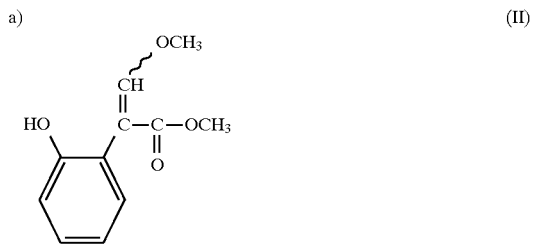

(II)

is reacted with pyrimidine derivatives of the formula (III)

(III)

in which

R and Y have the abovementioned meaning and

E represents an electron-attracting leaving group, if appropriate in the presence of a diluent and if appropriate in the presence of a reaction auxiliary; or b) the methyl 3-methoxy-2-(halogenopyrimidinyloxyphenyl)-acrylates obtained by process a), of the formula (Ia)

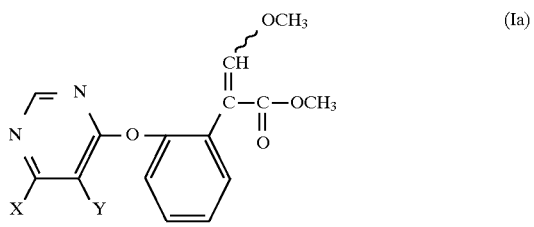

(Ia)

in which

X and Y independently of one another represent fluorine, chlorine, bromine or iodine, are reacted with compounds of the formula (IV)

Ar—Z—H (IV)

in which

Ar represents optionally substituted aryl or heteroaryl and

Z represents oxygen, sulfur or a group of the formula —S(O)—, —SO$_2$—, —NH—, —N(CH$_3$)—, —CH$_2$O— or —CH$_2$S—, if appropriate in the presence of a diluent and if appropriate in the presence of a reaction auxiliary and if appropriate in the presence of a catalyst.

Finally, it has been found that the new methyl 3-methoxy-2-phenyl-acrylates of the general formula (I) have a good activity against pests.

Surprisingly, the methyl 3-methoxy-2-phenyl-acrylates of the general formula (I) according to the invention show considerably better activity against phytopathogenic microorganisms compared with the methyl 3-methoxy-acrylates known from the prior art, such as, for example, the compound methyl 3-methoxy-2-(6-phenyl-2-pyridylthio)-acrylate or the compound methyl 3-methoxy-2-[N-(6-phenyl-2-pyridyl)-N-methyl-amino]-acrylate or the compound methyl 3-methoxy-2-[5-(4-chlorophenyl)-3-pyridyloxy]-acrylate, which are similar compounds chemically and/or from the point of view of their action.

Formula (I) provides a general definition of the methyl 3-methoxy-2-phenyl-acrylates according to the invention. Preferred compounds of the formula (I) are those in which Y represents fluorine, chlorine, bromine or iodine, R represents fluorine, chlorine, bromine, iodine or a radical of the formula Ar—Z—, in which Ar represents aryl having 6 to 10 carbon atoms which is optionally monosubstituted or polysubstituted by identical or different substituents, or represents heteroaryl having 2 to 9 carbon atoms and 1 to 5 identical or different hetero atoms, and which is optionally monosubstituted or polysubstituted by identical or different substituents and/or benzo-fused, suitable substituents in each case being:

halogen, cyano, nitro, hydroxyl, amino, formyl, carbamoyl, thiocarbamoyl, in each case straight-chain or branched alkyl, alkoxy, alkylthio, alkylsulfinyl or alkylsulfonyl, each of which has 1 to 6 carbon atoms, in each case straight-chain or branched alkenyl or alkenyloxy, each of which has 2 to 6 carbon atoms, in each case straight-chain or branched halogenoalkyl, halogenoalkoxy, halogenoalkylthio, halogenoalkylsulfinyl or halogenoalkylsulfonyl, each of which has 1 to 6 carbon atoms and 1 to 13 identical or different halogen atoms, in each case straight-chain or branched halogenoalkenyl or halogenoalkenyloxy, each of which has 2 to 6 carbon atoms and 1 to 13 identical or different halogen atoms, in each case straight-chain or branched N-alkylamino, dialkylamino, alkylcarbonyl, alkylcarbonyloxy, alkoxycarbonyl, alkylsulfonyloxy, hydroximinoalkyl or alkoximinoalkyl, each of which has 1 to 6 carbon atoms in the individual alkyl moieties, or in each case divalent alkylene or dioxyalkylene, each of which has 1 to 6 carbon atoms and each of which is optionally monosubstituted or polysubstituted by identical or different substituents from the series comprising halogen and/or straight-chain or branched alkyl having 1 to 4 carbon atoms and/or straight-chain or branched halogenoalkyl having 1 to 4 carbon atoms and 1 to 9 identical or different halogen atoms, or cycloalkyl having 3 to 7 carbon atoms, 3- to 7-membered heterocyclyl having 2 to 6 carbon atoms and 1 to 3 identical or different hetero atoms—in particular nitrogen, oxygen and/or sulfur—, and phenyl, phenoxy, benzyl, benzyloxy, phenylethyl or phenylethyloxy, each of which is optionally monosubstituted or polysubstituted in the phenyl moiety by identical or different substituents from the series comprising halogen and/or straight-chain or branched alkyl having 1 to 4 carbon atoms and/or straight-chain or branched halogenoalkyl having 1 to 4 carbon atoms and 1 to 9 identical or different halogen atoms and/or straight-chain or branched alkoxy having 1 to 4 carbon atoms and/or straight-chain or branched halogenoalkoxy having 1 to 4 carbon atoms and 1 to 9 identical or different halogen atoms, and Z represents oxygen, sulfur or a group of the formula —S(O)—, —SO$_2$—, —NH—, —N(CH$_3$)—, —CH$_2$O, or —CH$_2$S—.

Particularly preferred compounds of the formula (I) are those in which

Y represents fluorine or chlorine,

R represents fluorine, chlorine, bromine or a radical of the formula Ar—Z—, in which Ar represents aryl having 6 or 10 carbon atoms which is optionally monosubstituted to pentasubstituted by identical or different substituents, or represents heteroaryl having 2 to 9 carbon atoms and 1 to 3 identical or different hetero atoms—in particular nitrogen, oxygen and/or sulfur—, and which is optionally monosubstituted to tetrasubstituted by identical or different substituents and/or benzo-fused, suitable substituents in each case being:

halogen, cyano, nitro, hydroxyl, amino, formyl, carbamoyl, thiocarbamoyl, in each case straight-chain or branched alkyl, alkoxy, alkylthio, alkylsulfinyl or alkylsulfonyl, each of which has 1 to 4 carbon atoms, in each case straight-chain or branched alkenyl or alkenyloxy, each of which has 2 to 4 carbon atoms, in each case straight-chain or branched halogenoalkyl, halogenoalkoxy, halogenoalkylthio, halogenoalkylsulfinyl or halogenoalkylsulfonyl, each of which has 1 to 4 carbon atoms and 1 to 9 identical or different halogen atoms, in each case straight-chain or branched halogenoalkenyl or halogenoalkenyloxy, each of which has 2 to 4 carbon atoms and 1 to 9 identical or different halogen atoms, in each case straight-chain or branched N-alkylamino, dialkylamino, alkylcarbonyl, alkylcarbonyloxy, alkoxycarbonyl, alkylsulfonyloxy, hydroximinoalkyl or alkoximinoalkyl, each of which has 1 to 4 carbon atoms in the individual alkyl moieties, or in each case divalent alkylene or dioxyalkylene, each of which has 1 to 4 carbon atoms and each of which is optionally monosubstituted or polysubstituted by identical or different substituents from the series comprising halogen and/or straight-chain or branched alkyl having 1 to 3 carbon atoms and/or straight-chain or branched halogenoalkyl having 1 to 3 carbon atoms and 1 to 7 identical or different halogen atoms, or cycloalkyl having 3 to 6 carbon atoms, 5- to 7-membered, saturated heterocyclyl having 4 to 6 carbon atoms and 1 or 2 identical or different hetero atoms—in particular nitrogen, oxygen and/or sulfur—, and phenyl, phenoxy, benzyl, benzyloxy, phenylethyl or phenylethyloxy, each of which is optionally monosubstituted to trisubstituted in the phenyl moiety by identical or different substituents from the series comprising halogen and/or straight-chain or branched alkyl having 1 to 3 carbon atoms and/or straight-chain or branched halogenoalkyl having 1 to 3 carbon atoms and 1 to 7 identical or different halogen atoms and/or straight-chain or branched alkoxy having 1 to 3 carbon atoms and/or straight-chain or branched halogenoalkoxy having 1 to 3 carbon atoms and 1 to 7 identical or different halogen atoms, and Z represents oxygen, sulfur or a group of the formula —S(O)—, —SO$_2$—, —NH—, —N(CH$_3$)—, —CH$_2$O, or —CH$_2$S—.

Very particularly preferred compounds of the formula (I) are those in which

Y represents fluorine or chlorine,

R represents chlorine, bromine or a radical of the formula —Ar—Z— in which

Ar represents phenyl or naphthyl, each of which is optionally monosubstituted to trisubstituted by identical or different substituents, or represents furanyl, thienyl, pyrrolyl, oxazolyl, thiazolyl, isoxazolyl, isothiazolyl, pyrazolyl, imidazolyl, oxadiazolyl, thiadiazolyl, triazolyl, pyridyl, pyridazinyl, pyrimidinyl, pyrazinyl or triazinyl, each of which is optionally monosubstituted to trisubstituted by identical or different substituents and/or benzo-fused, suitable substituents in each case being:

fluorine, chlorine, bromine, hydroxyl, cyano, nitro, amino, formyl, carbamoyl, thiocarbamoyl, methyl, ethyl, n- or i-propyl, n-, i-, s- or t-butyl, methoxy, ethoxy, n- or i-propoxy, n-, i-, s- or t-butoxy, methylthio, ethylthio, methylsulfinyl, methylsulfonyl, allyl, butenyl, allyloxy, butenyloxy, trifluoromethyl, trifluoromethoxy, trifluoromethylthio, trifluoromethylsulfinyl, trifluoromethylsulfonyl, dimethylamino, diethylamino, acetyl, acetoxy, methylsulfonyloxy, ethylsulfonyloxy, methoxycarbonyl, ethoxycarbonyl, hydroximinomethyl, hydroximinoethyl, methoximinomethyl, methoximinoethyl, ethoximinomethyl, ethoximinoethyl, propane-1,3-diyl, butane-1,4-diyl, dioxymethylene, dioxyethylene, dioxypropylene, difluorodioxymethylene, tetrafluorodioxyethylene, cyclopropyl, cyclopentyl, cyclohexyl, 1-pyrrolidinyl, 1-piperidinyl, 1-perhydroazepinyl, 4-morpholinyl, or phenyl, phenoxy, benzyl or benzyloxy, each of which is optionally monosubstituted to trisubstituted by identical or different substituents from the series comprising fluorine, chlorine, bromine, methyl, ethyl, methoxy, ethoxy, trifluoromethyl and/or trifluoromethoxy, and Z represents oxygen, sulfur or a group of the formula —S(O)—, —SO$_2$—, —NH—, —N(CH$_3$)—, —CH$_2$O— or —CH$_2$S—.

The following methyl 3-methoxy-2-phenyl-acrylates of the general formula (Ib) may be mentioned individually in addition to the compounds mentioned in the preparation examples:

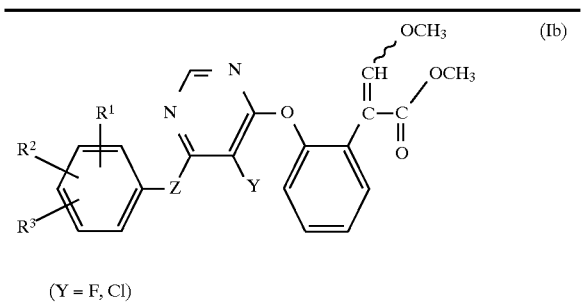

(Y = F, Cl)

| R$^1$ | R$^2$ | R$^3$ | Z |
|---|---|---|---|
| H | 2-CH$_3$ | 4-OCF$_3$ | —O— |
| H | 2-CH$_3$ | 4-O—CF$_2$—CF$_2$Cl | —O— |
| H | 2-CH$_3$ | 4-O—CF$_2$—CHF$_2$ | —O— |
| H | 2-Cl | 4-OCF$_3$ | —O— |
| H | H | 2-O—CHF$_2$ | —O— |
| H | 2-CH$_3$ | 4-OCF$_3$ | —O— |
| H | 2-CH$_3$ | 4-O—CF$_2$—CF$_2$Cl | —O— |
| H | 2-CH$_3$ | 4-O—CF$_2$—CHF$_2$ | —O— |
| H | 3,4-O—CF$_2$—CF$_2$—O— | | —O— |
| H | 3,4-CF$_2$—O—CF$_2$—O— | | —O— |
| H | 3,4-CF$_2$—O—CF$_2$— | | —O— |
| H | 3,4-O—CF$_2$—CH$_2$—O— | | —O— |
| H | 3,4-O—CF$_2$—CFCl—O— | | —O— |
| H | 3,4-O—CF$_2$—CHF—O— | | —O— |
| H | 3,4-CF$_2$—CHF—O— | | —O— |
| H | 3,4-O—CF$_2$—O— | | —O— |
| H | 3,4-O—CF$_2$—CF$_2$—O— | | —O— |
| H | 3,4-CF$_2$—O—CF$_2$—O— | | —O— |
| H | 3,4-CF$_2$—O—CF$_2$— | | —O— |
| H | 3,4-O—CF$_2$—CH$_2$—O— | | —O— |
| H | 3,4-O—CF$_2$—CFCl—O— | | —O— |
| H | 3,4-O—CF$_2$—CHF—O— | | —O— |
| H | 3,4-CF$_2$—CHF—O— | | —O— |
| H | 3,4-O—CF$_2$—O— | | —O— |

If, for example, 5-chloro-4,6-difluoropyrimidine and methyl 2-(2-hydroxyphenyl)-3-methoxy-acrylate are used as starting substances, the course of the reaction of process (a) according to the invention can be represented by the following equation:

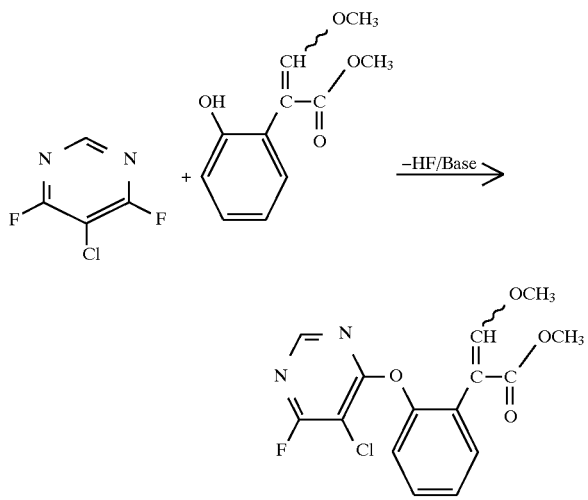

If, for example, methyl 2-[2-(5-chloro-6-fluoro-4-pyrimidinyloxy)-phenyl]-3-methoxy-acrylate and 2-hydroxybenzonitrile are used as starting substances, the course of the reaction of process (b) according to the invention can be represented by the following equation:

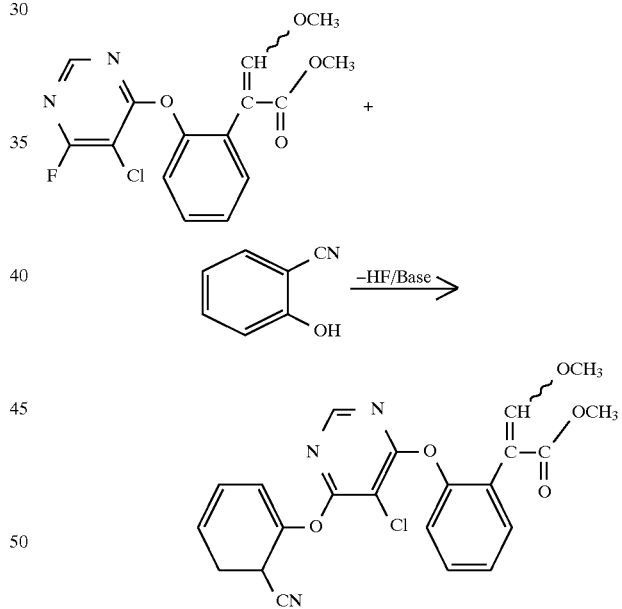

Formula (II) provides a definition of the 2-hydroxyphenyl-3-methoxyacrylate required as starting compound for carrying out process (a) according to the invention. The 2-hydroxyphenyl-3-methoxyacrylate of the formula (II) is known (cf. for example EP 242 081).

Formula (III) provides a general definition of the pyrimidine derivatives furthermore required as starting substances for carrying out process (a) according to the invention. In this formula (III), R and Y preferably represent those radicals which have already been mentioned in connection with the description of the compounds of the formula (I) according to the invention as being preferred for these substituents. E represents an electron-attracting leaving radical, preferably halogen, in particular fluorine, chlorine, bromine or iodine, or in each case optionally substituted alkylsulfonyloxy, alkoxysulfonyloxy or arylsulfonyloxy, such as, in particular, methanesulfonyloxy, trifluoromethanesulfonyloxy, methoxysulfonyloxy, ethoxysulfonyloxy or p-toluenesulfonyloxy.

The pyrimidine derivatives of the formula (III) are known (cf for example German offenlegungsschrift 1 931 640) or can be obtained by standard methods described in the literature.

Formula (Ia) provides a general definition of the methyl 3-methoxy-2-(halogeno-pyrimidinyloxy-phenyl)-acrylates required as starting substances for carrying out process (b) according to the invention. In this formula (Ia), X and Y independently of one another preferably represent fluorine, chlorine, bromine or iodine.

The methyl 3-methoxy-2-(halogenopyrimidinyloxy-phenyl)-acrylates of the formula (Ia) are compounds according to the invention.

Formula (IV) provides a general definition of the compounds furthermore required as starting substances for carrying out process (b) according to the invention. In this formula (IV), Ar and Z preferably represent those radicals which have already been mentioned in connection with the description of the compounds of the formula (I) according to the invention as being preferred for these substituents.

The compounds of the formula (IV) are generally known compounds of organic chemistry.

Suitable diluents for carrying out process (a) according to the invention are inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; nitriles, such as acetonitrile, propionitrile or benzonitrile; amides, such as N,N-dimethylformamide, N,N-diethylacetamide, N-methylformamide, N-methylpyrrolidone or hexamethylphosphoric triamide, or sulfoxides, such as dimethyl sulfoxide.

If appropriate, process (a) according to the invention can also be carried out in a two-phase system, such as, for example, water/toluene or water/dichloromethane, if appropriate in the presence of a suitable phase transfer catalyst. Examples of such catalysts which may be mentioned are: tetrabutylammonium iodide, tetrabutylammonium bromide, tetrabutylammonium chloride, tributylmethylphosphonium bromide, trimethyl-$C_{13}/C_{15}$-alkylammonium chloride, trimethyl-$C_{13}/C_{15}$-alkylammonium bromide, dibenzyldimethylammonium methylsulfate, dimethyl-$C_{12}/C_{14}$-alkylbenzylammonium chloride, dimethyl-$C_{12}/C_{14}$-alkylbenzylammonium bromide, tetrabutylammonium hydroxide, triethylbenzylammonium chloride, methyltrioctylammonium chloride, trimethylbenzylammonium chloride, 15-crown-5, 18-crown-6 or tris-[2-(2-methoxyethoxy)-ethyl]-amine.

Process (a) according to the invention is preferably carried out in the presence of a suitable reaction auxiliary. Suitable reaction auxiliaries are all customary inorganic or organic bases. These include, for example, the hydrides, hydroxides, amides, alcoholates, acetates, carbonates or hydrogen carbonates of alkaline earth metals or alkali metals, such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and also tertiary amines, such as trimethylamine, triethylamine, tributylamine, N,N-dimethylaniline, pyridine, N-methylpiperidine, N,N-dimethylaminopyridine, diazabicyclooctane, (DABCO), diazabicyclononene (DBN) or diazabicycloundecene (DBU).

When carrying out process (a) according to the invention, the reaction temperatures can be varied within a substantial range. In general, the process is carried out at temperatures between −30° C. and +120° C., preferably at temperatures between −20° C. and +60° C.

Process (a) according to the invention is conventionally carried out under atmospheric pressure. However, it is also possible to carry out the process under elevated or reduced pressure.

To carry out process (a) according to the invention, 1.0 to 10.0 mol, preferably 1.0 to 5.0 mol, of pyrimidine derivative of the formula (III) and, if appropriate, 1.0 to 5.0 mol, preferably 1.0 to 2.5 mol, of reaction auxiliary are generally employed per mol of methyl 2-hydroxyphenyl-3-methoxyacrylate of the formula (II). The reaction is carried out and the reaction products are worked up and isolated by known processes (cf. in this context also the Preparation Examples).

Suitable diluents for carrying out process (b) according to the invention are inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide, or sulfoxides, such as dimethyl sulfoxide.

Process (b) according to the invention is preferably carried out in the presence of a suitable reaction auxiliary. Suitable reaction auxiliaries are all customary inorganic or organic bases. These include, for example, the hydrides, hydroxides, amides, alcoholates, acetates, carbonates or hydrogen carbonates of alkaline earth metals or alkali metals, such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and also tertiary amines, such as trimethylamine, triethylamine, tributylamine, N,N-dimethylaniline, pyridine, N-methylpiperidine, N,N-dimethylaminopyridine, diazabicyclooctane, (DABCO), diazabicyclononene (DBN) or diazabicycloundecene (DBU).

If appropriate, process (b) according to the invention is also carried out in the presence of a suitable catalyst. Suitable catalysts are, in particular, copper(I) salts, such as, for example, copper(I) chloride. An addition of catalytic amounts of a suitable phase transfer catalyst, such as, for example, 15-crown-5, 18-crown-6 or tris-[2-(2-methoxyethoxy)-ethyl]-amine can be advantageous.

When carrying out process (b) according to the invention, the reaction temperatures can be varied within a substantial range. In general, the process is carried out at temperatures between −20° C. and +180°C., preferably at temperatures between 0° C. and +150° C.

Process (b) according to the invention is conventionally carried out under atmospheric pressure. However, it is also possible to carry out the process under elevated or reduced pressure.

To carry out process (b) according to the invention, 1.0 to 3.0 mol, preferably 1.0 to 1.5 mol, of compound of the formula (IV) and, if appropriate, 0.1 to 3.0 mol, preferably 0.5 to 1.5 mol, of base used as reaction auxiliary are generally employed per mol of methyl 3-methoxy-2-(halogenopyrimidinyloxy-phenyl)-acrylate of the formula (Ia). The reaction is carried out and the reaction products are worked up and isolated in each case analogously to known processes (cf. in this context for example EP 382 375 and the Preparation Examples).

The end products of the formula (I) are purified with the aid of customary processes, for example by column chromatography or by recrystallization. They are characterized with the aid of the melting point or, in the case of compounds which do not crystallize, with the aid of the refractive index or proton nuclear resonance spectroscopy ($^1$H-NMR).

The active compounds according to the invention have a powerful microbicidal activity and can be employed in practice for combating undesired microorganisms. The active compounds are suitable for use as plant protection agents, in particular as fungicides.

Fungicidal agents in plant protection are employed for combating *Plasmodiophoromycetes, Oomycetes, Chytridiomycetes, Zygomycetes, Ascomycetes, Basidiomycetes* and *Deuteromycetes.*

Some causative organisms of fungal diseases which come under the generic names listed above may be mentioned as examples, but not by way of limitation:

*Pythium* species, such as, for example, *Pythium ultimum;*
*Phytophthora* species, such as, for example, *Phytophthora infestans;*
*Pseudoperonospora* species, such as, for example, *Pseudoperonospora humuli* or *Pseudoperonospora cubense;*
*Plasmopara* species, such as, for example, *Plasmopara viticola;*
*Peronospora* species, such as, for example, *Peronospora pisi* or *Peronospora brassicae;*
*Erysiphe* species, such as, for example, *Erysiphe graminis;*
*Sphaerotheca* species, such as, for example, *Sphaerotheca fuliginea;*
*Podosphaera* species, such as, for example, *Podosphaera leucotricha;*
*Venturia* species, such as, for example, *Venturia inaequalis;*
*Pyrenophora* species, such as, for example, *Pyrenophora teres* or *Pyrenophora graminea* (conidia form: *Drechslera,* syn: *Helminthosporium*);
*Cochliobolus* species, such as, for example, *Cochliobolus sativus* (conidia form: *Drechslera,* syn: *Helminthosporium*);
*Uromyces* species, such as, for example, *Uromyces appendiculatus;*
*Puccinia* species, such as, for example, *Puccinia recondita;*
*Tilletia* species, such as, for example, *Tilletia caries;*
*Ustilago* species, such as, for example, *Ustilago nuda* or *Ustilago avenae;*
*Pellicularia* species, such as, for example, *Pellicularia sasakii;*
*Pyricularia* species, such as, for example, *Pyricularia oryzae;*
*Fusarium* species, such as, for example, *Fusarium culmorum;*
*Botrytis* species, such as, for example, *Botrytis cinerea;*
*Septoria* species, such as, for example, *Septoria nodorum;*
*Leptosphaeria* species, such as, for example, *Leptosphaeria nodorum;*
*Cercospora* species, such as, for example, *Cercospora canescens;*
*Alternaria* species, such as, for example, *Alternaria brassicae* and
*Pseudocercosporella* species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed particularly successfully for combating diseases in fruit and vegetable growing, such as, for example, against the causative organism of tomato blight (*Phytophthora infestans*) or against the causative organism of apple scab (*Venturia inaequalis*) or for combating cereal diseases, such as, for example, against the causative organism of powdery mildew of cereals (*Erysiphe graminis*) or against the causative organism of net blotch of barley (*Pyrenophora teres*) or against the causative organism of glume blotch of wheat (*Leptosphaeria nodorum*) or against *Fusarium* species in cereals or for combating rice diseases, such as, for example, against the causative organism of rice blast disease (*Pyricularia oryzae*). In addition, the active compounds according to the invention have good in-vitro activity.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. Suitable liquid solvents, are in the main: aromatics, such as xylene, toluene, alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, as well as water; by liquefied gaseous extenders or carriers are meant liquids which are gaseous at ambient temperature and under atmospheric pressure, for example aerosol propellants, such as halogenohydrocarbons as well as butane, propane, nitrogen and carbon dioxide; suitable solid carriers are: for example ground natural minerals, such as kaoline, clays, talc, chalk, quartz, attapulgite, montmorillonite or diatomaceous earth, and ground synthetic minerals, such as highly disperse silica, alumina and silicates; suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifying and/or foam-forming agents are: for example non-ionic and anionic emulsifiers, such as polyoxyethylene fatty acid esters, polyoxyethylene fatty alcohol ethers, for example alkylaryl polyglycol ethers, alkylsulfonates, alkylsulfates, arylsulfonates as well as albumen hydrolysis products; suitable dispersing agents are: for example lignin-sulfite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in their formulations, can also be used in the form of a mixture with known fungicides, bactericides, akaricides, nematicides or insecticides, for example to broaden the spectrum of action or to prevent the build-up of resistance. In many cases, synergistic effects can be observed.

The following are examples of suitable components for the mixtures:

Fungicides: 2-aminobutane; 2-anilino-4-methyl-6-cyclopropylpyrimidine; 2',6-dibromo-2-methyl-4'-trifluoromethoxy-4'-trifluoro-methyl-1,3-thiazole-5-carboxanilide; 2,6-dichloro-N-(4-trifluoromethylbenzyl) benzamide; (E)-2-methoxyimino-N-methyl-2-(2-phenoxyphenyl)acetamide; 8-hydroxyquinoline sulfate; methyl (E)-2-{2-[6-(2-cyanophenoxy)pyrimidin-4-yloxyphenyl}-3-methoxyacrylate; methyl (E)-methoximino [α-(o-tolyloxy)-o-tolyllacetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulfide, captafol, captan, carbendazim, carboxin, quinomethionate, chloroneb, chloropicrin, chlorothalonil, chlozolinat, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetylaluminum, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as copper hydroxide, copper naphthenate, copper oxychloride, copper sulfate, copper oxide, oxine copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulfur and sulfur preparations, tebucanazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram Bactericides: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulfate and other copper preparations.

Insecticides, acaricides, nematicides: abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, betacyluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184 699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etofenprox, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyraclofos, pyradaphenthion, pyresmethrin, pyrethrum, pyridaben, pyrimidifen, pyriproxifen, quinalphos, RH 5992, salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

A mixture with other known active compounds, such as herbicides, or with fertilizers and growth regulators, is also possible.

The active compounds can be applied as such, in the form of their formulations or in the use forms prepared from these compounds, such as ready-to-use solutions, suspensions, wettable powders, pastes, soluble powders, dusts and granules. They are applied in the customary manner, for example by pouring, spraying, atomizing, scattering, dusting, foaming, brushing on and the like. It is furthermore possible to apply active compounds by the ultra low volume method or to inject the active compound preparation, or the active compound itself, into the soil. The seed of the plants can also be treated.

In the treatment of parts of plants, the active compound concentrations in the use forms can be varied within a substantial range. In general, they are between 1 and 0.0001% by weight, preferably between 0.5 and 0.001% by weight.

In the treatment of seed, amounts of active compound of 0.001 to 50 g are generally required per kilogram of seed, preferably 0.01 to 10 g.

In the treatment of the soil, active compound concentrations of 0.00001 to 0.1% by weight, preferably 0.0001 to 0.02% by weight, are required at the site of action.

Preparation examples

EXAMPLE 1

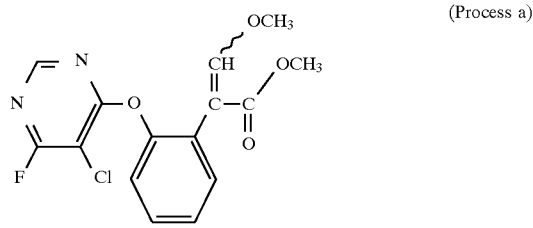
(Process a)

3 g (0.1 mol) of sodium hydride (80% in paraffin oil) are added in portions at 0° C. to a mixture of 15 g (0.1 mol) of 5-chloro-4,6-difluoropyrimidine and 20.8 g (0.1 mol) of methyl 2-(2-hydroxyphenyl)-3-methoxyacrylate in 100 ml of dimethylformamide, the batch is allowed to come to room temperature, and stirring is then continued for 24 hours. The reaction mixture is subsequently poured into water and extracted using ethyl acetate, and the extract is concentrated in vacuo. The residue is chromatographed on silica gel (eluent: diethyl ether/petroleum ether 1:1).

20.1 g (59.3% of theory) of methyl 2-[2-(5-chloro-6-fluoro-4-pyrimidinyloxy)-phenyl]-3-methoxy-acrylate of melting point 102° C. are obtained.

EXAMPLE 2

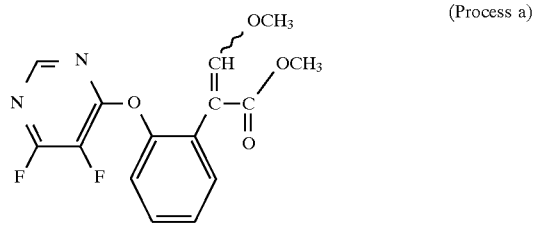
(Process a)

3.6 g (0.12 mol) of sodium hydride (80% in paraffin oil) are added in portions at 0° C. to a mixture of 16.1 g (0.12 mol) of 4,5,6-trifluoropyrimidine and 25.2 g (0.12 mol) of methyl 2-(2-hydroxyphenyl)-3-methoxy-acrylate in 120 ml of dimethylformamide, the batch is allowed to come to room temperature, and stirring is then continued for 2 hours. The reaction mixture is then poured into water and extracted using ethyl acetate, and the extract is concentrated in vacuo. The residue is chromatographed on silica gel (eluent: diethyl ether/petroleum ether 1:1).

3.6 g (9.6% of theory) of methyl 2-[2-(5,6-difluoro-4-pyrimidinyloxy)-phenyl]-3-methyloxy-acrylate of melting point 69° C. are obtained.

EXAMPLE 3

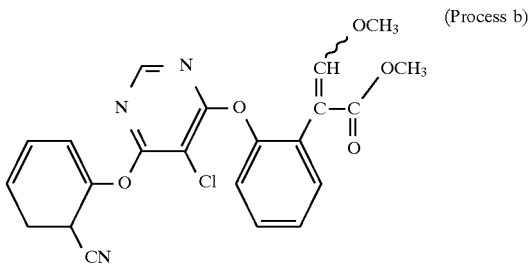
(Process b)

0.75 g (0.025 mol) of sodium hydride (80% in paraffin oil) is added in portions at 0° C. to a solution of 8.46 g (0.025 mol) of methyl 2-[2-(5-chloro-6-fluoro-4-pyrimidinyloxy)-phenyl]-3-methoxy-acrylate (Ex. 1) and 3 g (0.025 mol) of 2-hydroxybenzonitrile in 50 ml of dimethylformamide, and stirring of the reaction mixture is continued for 16 hours at 25° C. The reaction mixture is subsequently poured into water and extracted with ethyl acetate, the extract is concentrated in vacuo. The residue is refluxed for 10 minutes in tert-butyl methyl ether and filtered.

8.9 g (81.4% of theory) of methyl 2-{2-[5-chloro-6-(2-cyanophenoxy)-4-pyrimidinyloxy]-phenyl}-3-methoxy-acrylate of melting point 159° C.–61° C. are obtained.

The following methyl 3-methoxy-2-phenyl-acrylates of the general formula (I) are obtained analogously and following the general information on the preparation:

![Formula I structure]

| Ex. no. | R | Y | Physical properties |
|---|---|---|---|
| 4 | ![phenoxy] | F | 1H-NMR*) 3.64(3H); 3.78(3H); 7.0–7.6(9H); 7.49 (1H); 8.05(1H) |
| 5 | ![2-cyanophenoxy] | F | 1H-NMR*) 3.65(3H); 3.76(3H); 7.26–7.44(6H); 7.51 (1H); 7.67–7.76(2H); 8.04(1H) |

-continued

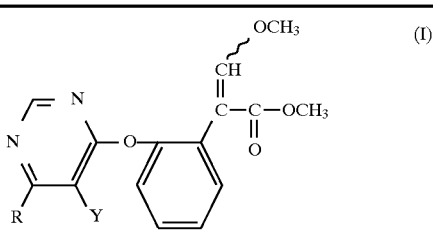

| Ex. no. | R | Y | Physical properties |
|---|---|---|---|
| 6 | ![R group with methoxyphenyl C=CH-OCH3, COOCH3] | F | $^1$H-NMR*) 3.50(6H); 3.74(6H); 7.27–7.51(8H); 7.55 (1H); 8.04(1H) |

*)The $^1$H-NMR spectra were recorded in deutero-chloroform (CDCl$_3$) or hexadeuterodimethyl sulfoxide (DMSO-d$_6$) using tetramethylsilane (TMS) as the internal standard. The data given is the chemical shift as δ value in ppm.

USE EXAMPLES

In the Use Examples which follow, the compounds listed below were used as comparison substances:

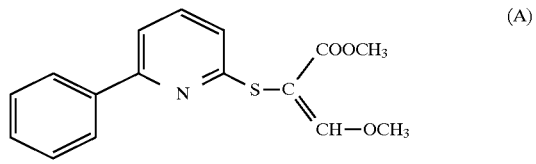

Methyl 3-methoxy-2-(6-phenyl-2-pyridylthio)-acrylate

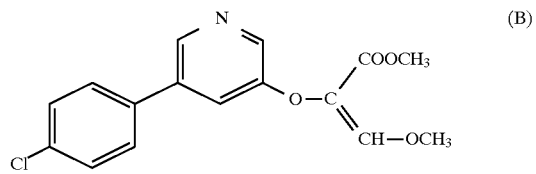

Methyl 3-methoxy-2-[5-(4-chlorophenyl)-3-pyridyloxy]-acrylate

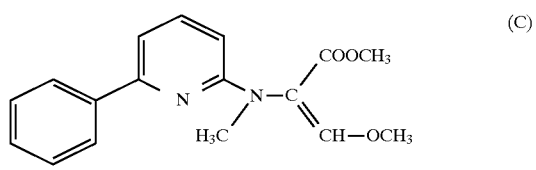

Methyl 3-methoxy-2-[N-(6-phenyl-2-pyridyl)-N-methylamino]-acrylate (all disclosed in EP 383 117)

EXAMPLE A

*Erysiphe* test (barley)/protective

Solvent: 10 parts by weight of N-methyl-pyrrolidone
Emulsifier: 0.6 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the dosage rate indicated. After the spray coating has dried on, the plants are dusted with spores of *Erysiphe graminis* f.sp. *hordei*.

The plants are placed in a greenhouse at a temperature of about 20° C. and a relative atmospheric humidity of about 80% in order to promote the development of powdery mildew pustules.

Evaluation is carried out 7 days after the inoculation.

In this text, a clearly superior activity compared with the prior art is shown, for example, by the compounds of Preparation Examples 4 and 5, which show a degree of effectiveness of over 80% at a dosage rate of active compound about 400 g/ha.

EXAMPLE B

*Pyrenophora teres* test (barley)/protective

Solvent: 10 parts by weight of N-methyl-pyrrolidone
Emulsifier: 0.6 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the dosage rate indicated. After the spray coating has dried on, the plants are sprayed with a conidia suspension of *Pyrenophora teres*. The plants remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compounds of Preparation Examples 4 and 5, which show a degree of effectiveness of up to 100% at a dosage rate of active compound about 400 g/ha.

EXAMPLE C

*Phytophthora* test (tomato)/protective

Solvent: 4.7 parts by weight of acetone Emulsifier: 0.3 part by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Phytophthora infestans*.

The plants are placed in an incubation cabin at a relative atmospheric humidity of about 100% and about 20° C.

Evaluation is carried out 3 days after the inoculation.

In this test, a clearly superior activity compared with the prior art is shown, for example, by the compounds of Preparation Examples 4 and 5, which show a degree of effectiveness of over 80% at an active compound concentration of 10 ppm.

EXAMPLE D

*Venturia* test (apple)/protective

Solvent: 4.7 parts by weight of acetone Emulsifier: 0.3 part by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of the apple scab causative organism Venturia inaequalis and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds of Preparation Examples 1, 3, 4, 5 and 6, which show a degree of effectiveness of up to 100% at an active compound concentration of 10 ppm.

EXAMPLE E

Pyricularia test (rice)/protective

Solvent: 12.5 parts by weight of acetone Emulsifier: 0.3 part by weight of alkylaryl polyglycol ether To produce a suitable preparation of active compound, 1 part by weight of active compound is mixed with the stated amount of solvent and emulsifier, and the concentrate is diluted with water to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds of Preparation Examples 4, 5 and 6, which show a degree of effectiveness of up to 100% at an active compound concentration of 0.025%.

We claim:

1. A methyl 3-methoxy-2-phenyl-acrylate of the formula (I)

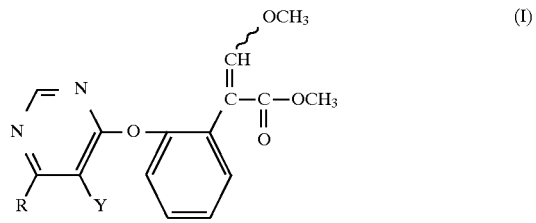

in which

Y represents fluorine, chlorine, bromine or iodine,

R represents fluorine, chlorine, bromine, iodine or a radical of the formula Ar—Z—, in which Ar represents aryl having 6 to 10 carbon atoms which is optionally monosubstituted to polysubstituted by identical or different substituents, or represents furanyl, thienyl, pyrrolyl, oxazolyl, thiazolyl, isoxazolyl, isothiazolyl, pyrazolyl, imidazolyl, oxadiazolyl, thiadiazolyl, triazolyl, pyridyl, pyridazinyl, pyrimidinyl, pyrazinyl or triazinyl, each of which is optionally monosubstituted or polysubstituted by identical or different substituents and/or benzo-fused, substituents in each case being selected from the group consisting of:

halogen, cyano, nitro, hydroxyl, amino, formyl, carbamoyl, thiocarbamoyl, in each case straight-chain or branched alkyl, alkoxy, alkylthio, alkylsulfinyl or alkylsulfonyl, each of which has 1 to 6 carbon atoms, in each case straight-chain or branched alkenyl or alkenyloxy, each of which has 2 to 6 carbon atoms, in each case straight-chain or branched halogenoalkyl, halogenoalkoxy, halogenoalkylthio, halogenoalkylsulfinyl or halogenoalkylsulfonyl, each of which has 1 to 6 carbon atoms and 1 to 13 identical or different halogen atoms, in each case straight-chain or branched halogenoalkenyl or halogenoalkenyloxy, each of which has 2 to 6 carbon atoms and 1 to 13 identical or different halogen atoms, in each case straight-chain or branched N-alkylamino, dialkylamino, alkylcarbonyl, alkylcarbonyloxy, alkoxycarbonyl, alkylsulfonyloxy, hydroximinoalkyl or alkoximinoalkyl, each of which has 1 to 6 carbon atoms in the individual alkyl moieties, or in each case divalent alkylene or dioxyalkylene, each of which has 1 to 6 carbon atoms and each of which is optionally monosubstituted or polysubstituted by identical or different substituents selected from the group consisting of halogen, straight-chain or branched alkyl having 1 to 4 carbon atoms, straight-chain or branched halogenoalkyl having 1 to 4 carbon atoms and 1 to 9 identical or different halogen atoms, cycloalkyl having 3 to 7 carbon atoms, 1-pyrrolidinyl, 1-piperidinyl, 1-perhydroazepinyl, 4-morpholinyl, and phenyl, phenoxy, benzyl, benzyloxy, phenylethyl or phenylethyloxy, each of which is optionally monosubstituted or polysubstituted in the phenyl moiety by identical or different substituents selected from the group consisting of halogen, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms, and straight-chain or branched halogenoalkoxy having 1 to 4 carbon atoms and 1 to 9 identical or different halogen atoms, and Z represents oxygen, sulfur or a group of the formula —S(O)—, —SO$_2$—, —NH—, —N(CH$_3$)—, —CH$_2$O—, or —CH$_2$—S—.

2. A compound of the formula (I) as claimed in claim 1, in which

Y represents fluorine or chlorine,

R represents fluorine, chlorine, bromine or a radical of the formula Ar—Z—, in which Ar represents aryl having 6 to 10 carbon atoms which is optionally monosubstituted to pentasubstituted by identical or different substituents, or represents furanyl, thienyl, pyrrolyl, oxazolyl, thiazolyl, isoxazolyl, isothiazolyl, pyrazolyl, imidazolyl, oxadiazolyl, thiadiazolyl, triazolyl, pyridyl, pyridazinyl, pyrimidinyl, pyrazinyl or triazinyl, each of which is optionally monosubstituted to tetrasubtituted by identical or different substituents and/or benzo-fused, substituents in each case being selected from the group consisting of:

halogen, cyano, nitro, hydroxyl, amino, formyl, carbamoyl, thiocarbamoyl, in each case straight-chain or branched alkyl, alkoxy, alkylthio, alkylsulfinyl or alkylsulfonyl, each of which has 1 to 4 carbon atoms, in each case straight-chain or branched alkenyl or alkenyloxy, each of which has 2 to 4 carbon atoms, in each case straight-chain or branched halogenoalkyl, halogenoalkoxy, halogenoalkylthio, halogenoalkylsulfinyl or halogenoalkylsulfonyl, each of which has 1 to 4 carbon atoms and 1 to 9 identical or different halogen atoms, in each case straight-chain or branched halogenoalkenyl or halogenoalkenyloxy, each of which has 2 to 4 carbon atoms and 1 to 9 identical or different halogen atoms, in each case straight-chain or branched N-alkylamino, dialkylamino, alkylcarbonyl, alkylcarbonyloxy, alkoxycarbonyl, alkylsulfonyloxy, hydroximinoalkyl or alkoximinoalkyl, each of which has 1 to 4 carbon atoms in the individual alkyl moieties, or in each case divalent alkylene or dioxyalkylene, each of which has 1 to 4 carbon atoms and each of which is optionally monosubstituted or poly-substituted by identical or different substituents selected from the group consisting of halogen, straight-chain or branched alkyl having 1 to 3 carbon atoms, straight-chain or branched halogenoalkyl having 1 to 3 carbon atoms and 1 to 7 identical or different halogen atoms, cycloalkyl having 3 to 6 carbon atoms, 1-pyrrolidinyl, 1-piperidinyl, 1-perhydroazepinyl, 4-morpholinyl, and phenyl, phenoxy, benzyl, benzyloxy, phenylethyl or phenylethyloxy, each of which is optionally monosubstituted to trisubstituted in the phenyl moiety by identical or different substituents selected from the group consisting of halogen, straight-chain or branched alkyl having 1 to 3 carbon atoms, straight-chain or branched halogenoalkyl having 1 to 3 carbon atoms and 1 to 7 identical or different halogen atoms, straight-chain or branched alkoxy having 1 to 3 carbon atoms, and straight-chain or branched halogenoalkoxy having 1 to 3 carbon atoms and 1 to 7 identical or different halogen atoms, and Z represents oxygen, sulfur or a group of the formula —S(O)—, —SO$_2$—, —NH—, —N(CH$_3$)—, —CH$_2$O—, or —CH$_2$S—.

3. A compound of the formula (I) as claimed in claim 1, in which

Y represents fluorine or chlorine,

R represents chlorine, bromine or a radical of the formula —Ar—Z— in which

Ar represents phenyl or naphthyl, each of which is optionally monosubstituted to trisubstituted by identical or different substituents, or represents furanyl, thienyl, pyrrolyl, oxazolyl, thiazolyl, isoxazolyl, isothiazolyl, pyrazolyl, imidazolyl, oxadiazolyl, thiadiazolyl, triazolyl, pyridyl, pyridazinyl, pyrimidinyl, pyrazinyl or triazinyl, each of which is optionally monosubstituted to trisubstituted by identical or different substituents and/or benzo-fused, substituents in each case being selected from the group consisting of:

fluorine, chlorine, bromine, hydroxyl, cyano, nitro, amino, formyl, carbamoyl, thiocarbamoyl, methyl, ethyl, n- or i-propyl, n-, i-, s- or t-, butyl, methoxy, ethoxy, n- or i-propoxy, n-, i-, s- or t-butoxy, methylthio, ethylthio, methylsulfinyl, methylsulfonyl, allyl, butenyl, allyloxy, butenyloxy, trifluoromethyl, trifluoromethoxy, trifluoromethylthio, trifluoromethylsulfinyl, trifluoromethylsulfonyl, dimethylamino, diethylamino acetyl, acetoxy, methylsulfonyloxy, ethylsulfonyloxy, methoxycarbonyl, ethoxycarbonyl, hydroximinomethyl, hydroximinoethyl, methoximino, methyl, methoximinoethyl, ethoximinomethyl, ethoximinoethyl, propane-1,3-diyl, butane-1,4-diyl, dioxymethylene, dioxyethylene, dioxypropylene, difluorodioxymethylene, tetrafluorodioxyethylene, cyclopropyl, cyclopentyl, cyclohexyl, 1-pyrrolidinyl, 1-piperidinyl, 1-perhydroazepinyl, 4-morpholinyl, or phenyl, phenoxy, benzyl or benzyloxy, each of which is optionally monosubstituted to trisubstituted by identical or different substituents selected from the group consisting of fluorine, chlorine, bromine, methyl, ethyl, methoxy, ethoxy, trifluoromethyl and/or trifluoromethoxy, and Z represents oxygen, sulfur or a group of the formula —S(O)—, —SO$_2$—, —NH—, —N(CH$_3$)—, —CH$_2$O—, or —CH$_2$S—.

4. A fungicidal composition comprising a fungicidally effective amount of a compound of formula (I) according to claim 1 and an extender.

5. A method of combatting fungi comprising subjecting the fungi, their environment, or a place from which it is desired to exclude such fungi to a fungicidally effective amount of a compound of formula (I) according to claim 1.

* * * * *